(12) United States Patent
Cordray

(10) Patent No.: US 12,145,008 B1
(45) Date of Patent: Nov. 19, 2024

(54) RESPIRATORY PROTECTION SYSTEM FOR SURGERY

(71) Applicant: Scott Cordray, Bixby, OK (US)

(72) Inventor: Scott Cordray, Bixby, OK (US)

( * ) Notice: Subject to any disclaimer, the term of this patent is extended or adjusted under 35 U.S.C. 154(b) by 804 days.

(21) Appl. No.: 17/210,115

(22) Filed: Mar. 23, 2021

Related U.S. Application Data

(60) Provisional application No. 63/065,064, filed on Aug. 13, 2020, provisional application No. 62/993,364, filed on Mar. 23, 2020.

(51) Int. Cl.
| | | |
|---|---|---|
| *A62B 18/08* | (2006.01) | |
| *A41D 13/11* | (2006.01) | |
| *A61B 90/50* | (2016.01) | |
| *A62B 7/10* | (2006.01) | |
| *A62B 7/12* | (2006.01) | |
| *A62B 9/00* | (2006.01) | |
| *A62B 18/00* | (2006.01) | |

(Continued)

(52) U.S. Cl.
CPC .......... *A62B 18/08* (2013.01); *A41D 13/1184* (2013.01); *A62B 7/10* (2013.01); *A62B 7/12* (2013.01); *A62B 9/00* (2013.01); *A62B 18/006* (2013.01); *A62B 18/02* (2013.01); *A62B 18/082* (2013.01); *A62B 23/02* (2013.01); *A61B 2090/502* (2016.02)

(58) Field of Classification Search
CPC ..... A62B 18/006; A62B 18/02; A62B 18/025; A62B 18/04; A62B 18/08; A62B 18/082; A62B 18/084; A62B 18/088; A62B 7/00; A62B 7/02; A62B 7/04; A62B 7/10; A62B 7/12; A62B 23/00; A62B 23/02; A62B 23/025; A62B 18/045; A41D 13/11; A41D 13/1153; A41D 13/1184; A41D 13/1218; A61B 2090/502; A42B 3/28; A42B 3/225; A42B 3/286; A61M 16/009; A61M 16/0093; B63C 11/12; B63C 11/14
See application file for complete search history.

(56) References Cited

U.S. PATENT DOCUMENTS

| | | | | |
|---|---|---|---|---|
| 3,955,570 | A | * 5/1976 | Hutter, III | A61B 90/40 128/863 |
| 5,042,474 | A | * 8/1991 | Williamson | A41D 13/1184 55/DIG. 35 |

(Continued)

FOREIGN PATENT DOCUMENTS

DE     102018100473 A1 *  7/2019  .......... A62B 18/006

OTHER PUBLICATIONS

Machine Translation of DE-102018100473-A1. Accessed from PE2E Search tool on Jan. 2024. (Year: 2019).*

*Primary Examiner* — Kendra D Carter
*Assistant Examiner* — Jaeick Jang
(74) *Attorney, Agent, or Firm* — Head, Johnson, Kachigian & Wilkinson, PC

(57) ABSTRACT

A respiratory protection system for use during surgery. The respiratory protection system may be a powered air purifying respirator, a supplied air respirator, or a self-contained breathing apparatus. The system may include an integrated surgical headlight and/or integrated surgical loupes. The system may further offer a face shield that fits very close to the wearer's eyes above the nasal dorsum, allowing use of the system while operating a microscope or the optics of a robotic surgery system.

6 Claims, 3 Drawing Sheets

(51) Int. Cl.
*A62B 18/02* (2006.01)
*A62B 23/02* (2006.01)

(56) References Cited

U.S. PATENT DOCUMENTS

| | | | | |
|---|---|---|---|---|
| 5,446,507 | A * | 8/1995 | Chang | G02B 7/002 |
| | | | | 351/158 |
| 7,028,688 | B1 * | 4/2006 | Grove | A62B 17/04 |
| | | | | 128/206.17 |
| 2003/0131846 | A1 * | 7/2003 | Campbell | A62B 18/08 |
| | | | | 128/206.17 |
| 2007/0163588 | A1 * | 7/2007 | Hebrank | A61M 16/0069 |
| | | | | 128/205.29 |
| 2011/0219506 | A1 * | 9/2011 | Uttrachi | A61F 9/067 |
| | | | | 2/8.6 |
| 2018/0311515 | A1 * | 11/2018 | Wilson | A61B 5/6803 |
| 2019/0118916 | A1 * | 4/2019 | Xiao | B63C 11/16 |
| 2020/0275724 | A1 * | 9/2020 | Jefferis | A42B 3/286 |

* cited by examiner

RESPIRATORY PROTECTION SYSTEM FOR SURGERY

CROSS REFERENCE

This application is based on and claims priority to U.S. Provisional Patent Application No. 62/993,364 filed Mar. 23, 2020 and U.S. Provisional Patent Application No. 63/065,064 filed Aug. 13, 2020.

BACKGROUND OF THE INVENTION

Field of the Invention

This invention relates generally to a respiratory protection system for use during surgery and more particularly, but not by way of limitation, to a respiratory protection system with integrated surgical headlight and/or surgical loupes.

Description of the Related Art

A novel coronavirus known as COVID-19 was first detected in 2019 and quickly spread into a worldwide pandemic. In the regions first affected, it was quickly determined that ENTs and ophthalmologists had a disproportionately high rate of infection. Recent data suggests that the COVID-19 virus is aerosolized when the mucous membranes are breached, especially during endonasal procedures such as functional endoscopic sinus surgeries. This may leave everyone in the room where the procedure is performed vulnerable to infection, with the virus potentially lingering in the air for hours. The N95 mask do not provide adequate protection against COVID-19. The spread of infection has been controlled, however, through the use of powered air purifying respirators (PAPRs) by medical personnel. PAPRs are typically a full face mask that not only filters the air breathed by the wearer, they also protect the wearer's eyes more fully than regular goggles.

The problem with using PAPRs during surgery is that they prevent the use of surgical headlights and surgical loupes. A standard PAPR fits similarly to a helmet with a sealed face shield and an integrated purified air supply. Surgical headlights are typically worn on a surgeon's head, often being mounted to a headpiece that encircles the surgeon's head. Such a head-mounted apparatus cannot fit either under or over a standard PAPR. Likewise, surgical loupes are typically worn on glasses, which similarly would not fit either under or over a standard PAPR.

Furthermore, the face shield of a standard PAPR is typically offset from the user's face. This may make use of a microscope or the optics for a robotic surgical system difficult, if not impossible.

Based on the foregoing, it is desirable to provide a respiratory protection system for use during surgery that integrates headlights and/or surgical loupes.

It is further desirable to provide a respiratory protection system with a face shield that fits close to the wearer's eyes, allowing the user to operate a microscope or robotic surgical system.

It is further desirable for the respiratory protection system to filter air exhaled by the wearer to protect others.

Figure 1:
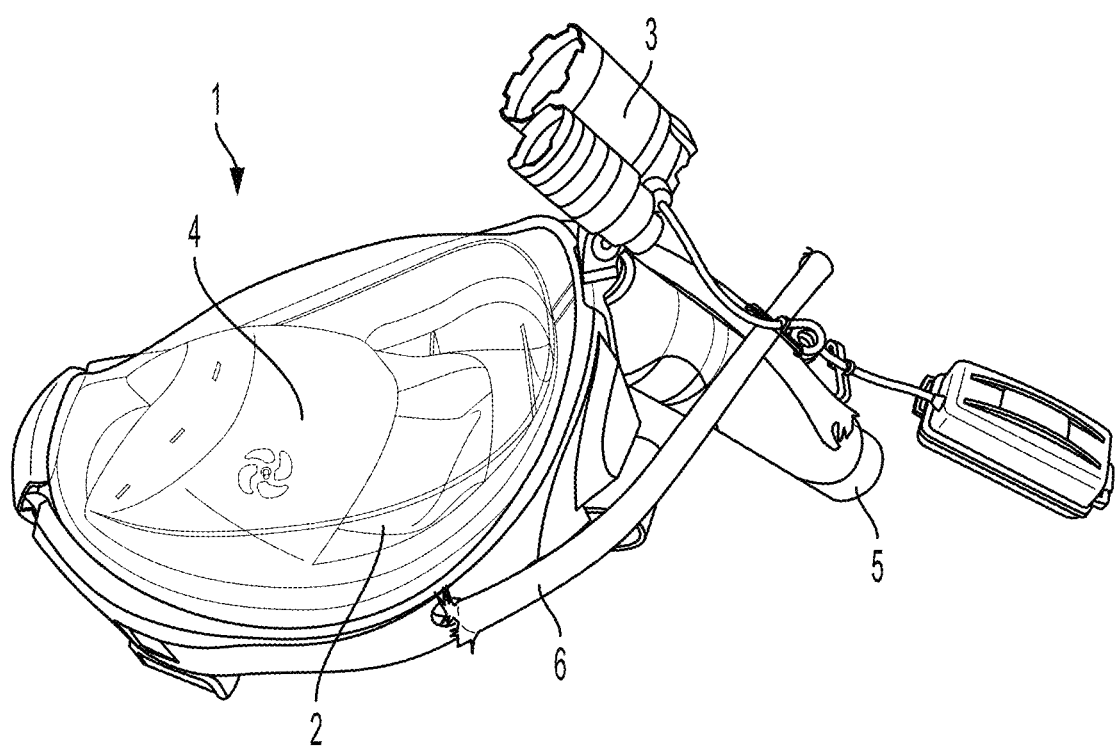
FIG. 1 is a perspective view of a respiratory protection system with integrated surgical headlight of the present invention.

Other advantages and features will be apparent from the following description and from the claims.

DETAILED DESCRIPTION OF THE INVENTION

The devices and methods discussed herein are merely illustrative of specific manners in which to make and use this invention and are not to be interpreted as limiting in scope.

While the devices and methods have been described with a certain degree of particularity, it is to be noted that many modifications may be made in the details of the construction and the arrangement of the devices and components without departing from the spirit and scope of this disclosure. It is understood that the devices and methods are not limited to the embodiments set forth herein for purposes of exemplification.

In general, in a first aspect, the invention relates to a respiratory protection system 1. The system 1 may comprise a powered air purifying respirator (PAPR), supplied air respirator (continuous flow respirator), or other self-contained breathing apparatus 2. The system may further comprise one or more integrated surgical accessories 3, which may include an integrated surgical headlight, as shown, and/or integrated surgical loupes.

The PAPR 2 may include a sealable face shield 4 and an intake hose 5 connected on one end to the face shield 4 and on the other to an air supply, such as a powered fan and battery, which may be mounted on a belt. The hose 5 may be equipped with a filter, such as a HEPA filter, such that ambient air may be pulled by the fan into the hose 5 where it is filtered prior to entering the face shield 4.

Figure 2:
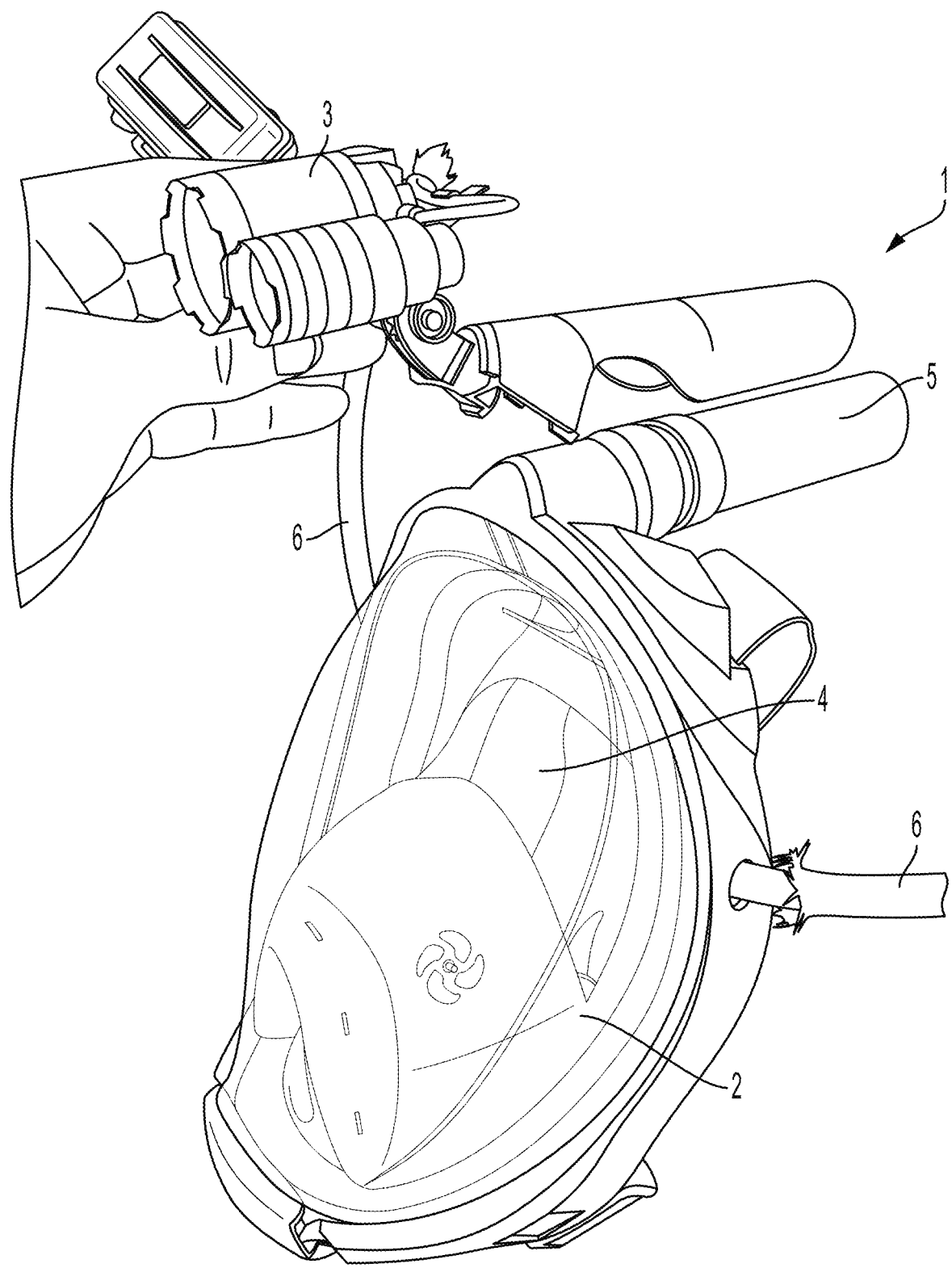
FIG. 2 is an exploded view of the respiratory protection system with integrated surgical headlight.
Figure 3:
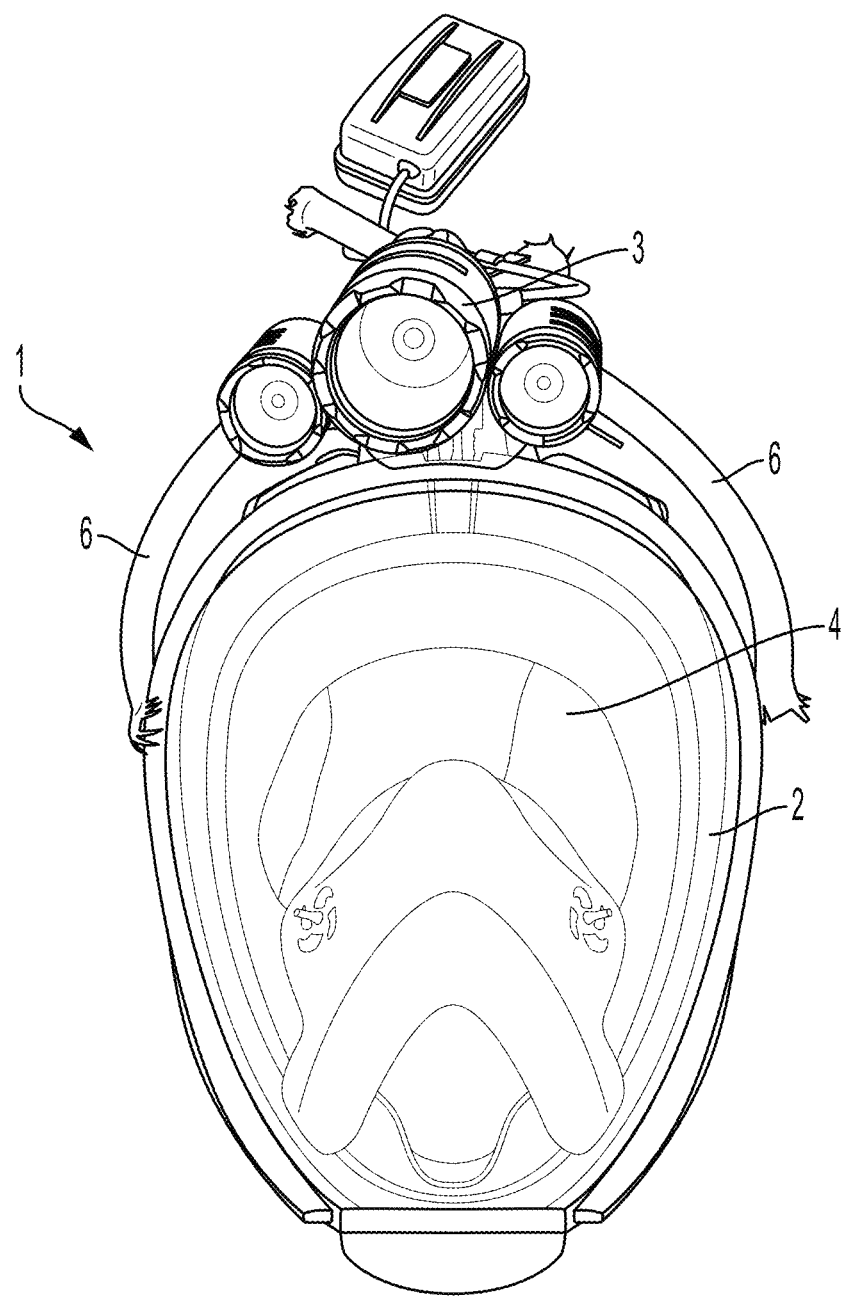
FIG. 3 is a front view of the respiratory protection system with integrated surgical headlight.

The integrated surgical accessories 3 may clip or snap onto the intake hose 5 at the top of the face shield 4, as shown in FIG. 2. The system 1 may further comprise one or more exhalation ports 6. The exhalation ports 6 may be capable of conveying air exhaled by the user out of the system. The exhalation ports 6 may be equipped with filters, such as HEPA filters, to filter the exhaled air prior to discharge. The exhalation ports 6 may be hoses that discharge behind the user's head, thus keeping the discharged air from blowing into a sterile field.

Additionally or alternately, the face shield 4 may come down to the nasal dorsum very close to the user's eyes. This may allow the user to operate a microscope or the optics of a robotic surgical system while wearing the face shield. During such use, additional light may not be needed, and thus the surgical headlight may be omitted.

By providing HEPA filtration on both the inhalation and exhalation side of the PAPR 2, the system 1 may protect both the wearer from inhaling aerosols exhaled by others in the vicinity and the others from inhaling aerosols exhaled by the wearer. The sealable face shield 4 may further protect the wearer from infection through the wearer's eyes.

Whereas, the devices and methods have been described in relation to the drawings and claims, it should be understood that other and further modifications, apart from those shown or suggested herein, may be made within the spirit and scope of this invention.

What is claimed is:

1. A respiratory protection system for surgery comprising:
   a sealable face shield;
   an air supply;

an intake hose with a first end connected to the face shield and a second end connected to the air supply;

one or more exhalation ports capable of conveying air exhaled by a user out of the system;

one or more filters to filter the exhaled air prior to discharge; and one or more surgical accessories, where the one or more surgical accessories comprise:

an integrated surgical headlight; and/or one or more integrated surgical loupes;

where the one or more exhalation ports are hoses, that discharge rearward of the system, where the one or more exhalation ports each comprise a terminal end defined by an orifice, such that when the face shield is worn by the user, the orifice is above the head of the user and discharged air is blown behind and above the head of the user rather than into a sterile field in front of the user.

2. The respiratory protection system of claim 1 where the air supply is a powered fan and battery, where the powered fan and the battery are capable of being mounted on a belt.

3. The respiratory protection system of claim 1 where the intake hose is equipped with a filter such that an ambient air may be pulled by a fan into the intake hose where it is filtered prior to entering the face shield.

4. The respiratory protection system of claim 3 where the filter is a HEPA filter.

5. The respiratory protection system of claim 1 where the one or more surgical accessories are removably attached to the hose atop the face shield.

6. The respiratory protection system of claim 1 where the face shield comes down to the user's nasal dorsum such that the system is capable of allowing the user to wear the face shield while operating a microscope or optics of a robotic surgical system.

* * * * *